United States Patent [19]

Wright et al.

[11] Patent Number: 4,882,324

[45] Date of Patent: Nov. 21, 1989

[54] ESSENTIALLY PURE ACID HYDROXYL LIGAND ALUMINUM COMPLEXES AND THEIR PREPARATION

[76] Inventors: Arthur P. G. Wright, 98 Spragg Cir., Markham, Ontario, Canada, L3P 5C2; Betty P. L. Wen, 89 Bushmills Sq., Scarborough, Ontario, Canada, M1V 1K5; Terry G. Schenck, 74 Water Wheelway, Willowdale, Ontario, Canada, M2H 3E5; Antonina Maron, 12 Willowmount Dr., Scarborough, Ontario, Canada, M1L 1Y1

[21] Appl. No.: 201,669

[22] Filed: Jun. 2, 1988

Related U.S. Application Data

[62] Division of Ser. No. 937,155, Dec. 2, 1986, Pat. No. 4,772,724.

[30] Foreign Application Priority Data

Nov. 21, 1986 [CA] Canada ................................ 523590

[51] Int. Cl.$^4$ ...................... A61K 31/33; A61K 37/44

[52] U.S. Cl. .................................. 514/191; 514/561; 514/567; 514/569

[58] Field of Search ............... 514/191, 569, 159, 561, 514/567

[56] References Cited

FOREIGN PATENT DOCUMENTS

| | | | |
|---|---|---|---|
| 57-062262 | 4/1982 | Japan ................................ | 514/191 |
| 57-062263 | 4/1982 | Japan ................................ | 514/191 |
| 57-062264 | 4/1982 | Japan ................................ | 514/191 |
| 57-062265 | 4/1982 | Japan ................................ | 514/191 |
| 57-062266 | 4/1982 | Japan ................................ | 514/191 |

*Primary Examiner*—Frederick E. Waddell
*Attorney, Agent, or Firm*—Daniel A. Scola, Jr.; Craig M. Bell; Charles A. Gaglia, Jr.

[57] ABSTRACT

Essentially pure acid hydroxyl ligand aluminum complexes useful as antacids are prepared by first reacting an acid hydroxyl ligand with an aluminum alkoxide under anhydrous conditions to form an intermediate and further reacting the intermediate with water, these complexes are useful as antacids and as such in the treatment of hyperacidity.

7 Claims, No Drawings

ESSENTIALLY PURE ACID HYDROXYL LIGAND ALUMINUM COMPLEXES AND THEIR PREPARATION

This is a divisional of Ser. No. 937,155 filed Dec. 2, 1986, U.S. Pat. No. 4,772,724.

FIELD OF THE INVENTION

This invention relates to essentially pure, acid hydroxyl ligand aluminum complexes, their preparation and use as antacids in the treatment of hyperacidity.

BACKGROUND OF THE INVENTION

Antacid preparations for oral administration and reduction of gastric acidity have long been known. Gastric antacids are generally classified as absorbable and nonabsorbable, depending on the amount of systemic absorption of the cation responsible for the neutralization of gastric hydrochloric acid. The preferred gastric antacids are compounds whose cationic portion is not absorbed from the intestine and that raises the pH of the gastric contents only to about 5. This class of compounds is referred to as nonabsorbable buffer antacids. Aluminum compounds are generally considered nonabsorbable. More recent studies, however, indicate at least some systemic aluminum absorption does occur. Aluminum compounds have many of the desirable properties of an ideal buffer antacid. These include a good buffering ability, the absence of acid rebound and the absence of gas producing components. Nonaluminum antacids do not possess all of these desirable properties of aluminum compounds and are therefore less desirable as antacids.

The effectiveness of aluminum containing antacids for the treatment of peptic ulcers has been clinically documented and is widely accepted. There are, however, certain side effects of using this type of antacid of which constipation is the most common.

Constipation results when aluminum inhibits contraction of the smooth musculature delaying stomach emptying thus resulting in slight blockage. In addition, aluminum interacts in the intestine with anions such as phosphate and carbonate and forms insoluble compounds. The biological consequences of the interaction of aluminum with phosphate following the intake of aluminum hydroxide are well known.

The primary event is precipitation of phosphate in the small intestine leading to elevated fecal phosphate. This reduces the availability of phosphorus for systemic absorption and may lead to a lowering of serum phosphate levels. Because of the importance of phosphate, the body has a series of homeostatic mechanisms to overcome this reduction in available phosphate. Under conditions of normal phosphate levels, the input into serum is balanced by its rate of removal. The sources of input are intestinal absorption, bone mineral resorption, renal phosphate reabsorption and transfer from soft tissue. Sources of removal include intestinal secretion, bone mineralization, glomerular (kidney) filtration and transfer to soft tissue. When any one of these factors is perturbed, the other processes are modified to restore balance. Thus, when available phosphate decreases, processes such as bone resorption and renal reabsorption increase considerably. The bone resorption process, in addition to supplying phosphate, also resorbs calcium leading to elevated urinary calcium excretion. Thus, indirectly, aluminum interferes with calcium balance by causing calcium loss and it has been suggested that the demineralization process may be accelerated by aluminum.

The following clinical changes have been reported, in normal patients, in which the effects of aluminum on mineral metabolism have been studied.
1. Increase in fecal phosphorus and calcium.
2. Decrease in serum phosphorus.
3. Decrease in urinary phosphorus.
4. Increase in urinary calcium and magnesium.
5. Increase in renal reabsorption of phosphorus.

The combination of these biochemical perturbations is considered to be a contributing factor in bone loss.

A large number of commercial antacids are available which contain aluminum compounds. Most of these products contain aluminum hydroxide alone or in combination with other basic compounds such as magnesium hydroxide, calcium carbonate, sodium carbonate and the like. Other aluminum containing compounds include aluminum phosphate, dihydroxy aluminum aminoacetate, aluminum carbonate, and magaldrate, a chemical combination of aluminum hydroxide and magnesium hydroxide. None of these products overcome the undesirable mineral metabolic side effects of aluminum containing antacids.

It would, therefore, be desirable to develop an antacid composition having the advantageous properties of aluminum antacids while minimizing the undesirable side effects.

SUMMARY OF THE INVENTION

A procedure for preparing essentially pure acid hydroxyl ligand and aluminum complexes having the formula:

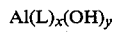
$$Al(L)_x(OH)_y$$

wherein:
X=0.5, 1
Y=2, and
L is an acid hydroxyl ligand
has been discovered. This has been achieved by first reacting an aluminum alkoxide of the general formula $AL(OR)_3$ in the presence of an anhydrous solvent with an acid hydroxyl ligand in an amount of from about 0.5 mole to about 1 mole of acid hydroxyl ligand per mole of aluminum alkoxide to form an intermediate.

Further reacting the intermediate with water in an amount of about 2 moles per mole of aluminum alkoxide, the amount of acid hydroxyl ligand and water being sufficient to replace all of the alkoxy groups of the aluminum alkoxide, removing the solvent and recovering the products.

DETAILED DESCRIPTION

In particular, it has been found that essentially pure acid hydroxyl ligand and aluminum complexes having an acid neutralization capacity of at least 5 mEq/g and the formula:

$$Al(L)_x(OH)_y$$

wherein:
X=0.5, 1
Y=2 and
L is an acid hydroxyl ligand
can be prepared.

The essentially pure acid hydroxyl ligand and aluminum complexes of the present invention, have a high acid neutralization capacity (ANC), are fast acting, long lasting, pleasant tasting, easily formulated in solid or liquid dosage forms, have virtually no sodium content, and precipitate less phosphate from the gastrointestinal (GI) tract than aluminum hydroxide.

While the invention is not to be limited to theoretical considerations, it is believed that absorption of aluminum in the GI tract is lessened by increasing the molecular size of the aluminum complex. In addition, it is believed that phosphate precipitation would be lessened by complexing the aluminum with appropriate acid hydroxyl ligands so that the availability of aluminum for interaction with phosphate is reduced.

The aluminum alkoxide and acid hydroxyl ligand are first reacted in the absence of water in an anhydrous solvent to form an intermediate, further reacting the intermediate with water such that the amount of acid hydroxyl ligand and water being sufficient to replace all of the alkoxy groups of the aluminum alkoxide, removing the solvent and recovering the product.

The stoichiometry of the reaction is believed to be as follows:
1. $Al(OR)_3 + xL \rightarrow$ Intermediate
2. Intermediate $+ yH_2O \rightarrow Al(L)_x(OH)_y$ wherein
$X = 0.5, 1$
$Y = 2$
$L =$ an acid hydroxyl ligand and
$R =$ a carbon chain having 1 to about 8 carbon atoms.

Preferably the aluminum alkoxide is reacted in the presence of an anhydrous solvent with an acid hydroxyl ligand in an amount of from about 0.5 mole to about 1 mole of acid hydroxyl ligand per mole of aluminum alkoxide to form an intermediate, and further reacting the intermediate with water in an amount of from about 1 mole to about 2 moles per mole of aluminum alkoxide, the amount of acid hydroxyl ligand and water being sufficient to replace all of the alkoxy groups of the aluminum alkoxide, removing the solvent and recovering the product.

The aluminum alkoxide preferably has the formula $Al(OR)_3$, where R has a carbon chain of about 1 to about 8 carbon atoms. The chains may be either straight or branched. Examples of such alkoxides are methoxide, ethoxide, isopropoxide, propoxide, butoxide, isobutoxide, amyloxide, hexoxide, octoxide, 2-ethyl-butoxide, 2-ethyl-hexoxide and the like. The preferred alkoxide is aluminum isopropoxide.

Throughout the specification, examples and claims, the term "acid hydroxyl ligand" is defined as a carbon containing compound having at least 3 carbon atoms and at least three donating atoms to provide strong complexation with aluminum at least two of which are oxygen one in the form of a carboxylate, a second is in the form of a hydroxyl and the third and additional donating atoms are selected from the group consisting of nitrogen, sulfur, and oxygen. The carbon containing compound can be in the form of an alkane, alkene, cycloalkane, cycloalkene and aromatic hydrocarbon. The nitrogen atom can be in the form of an amine such as a primary, secondary, tertiary and heterocyclic amine. The oxygen atom may be in the form of an acidic group such as a carboxylate, hydroxyl and aromatic hydroxyl. The sulfur atom may be in the form of a thiol. The acid hydroxyl ligand may contain additional donating atoms such as hydroxyl, carboxylic, amino, aromatic hydroxyl, thiol and the like. Donating atoms are those atoms which have an electron pair and act as a base whereas the aluminum atom accepts the electron pair and functions as an acid.

Acid amine ligands useful in the present invention are illustrated by the following nonlimiting list: serine, homoserine, threonine, tyrosine, hydroxyproline, pamoic acid, bicine, tricine, hydroxylysine and the like.

Exemplary essentially pure acid hydroxyl ligand aluminum complexes are illustrated by the following nonlimiting list: monoaluminum bicine, monoaluminum tricine, monoaluminum threonine, monoaluminum pamoic acid and dialuminum pamoic acid.

In a preferred embodiment, the aluminum alkoxide is reacted in the presence of an anhydrous solvent with an acid hydroxyl ligand in an amount of from about 0.5 mole to about 1 mole of acid hydroxyl ligand per mole of aluminum alkoxide for about 30 to about 90 minutes at about 40° C. to about 90° C. to form an intermediate, then water is added dropwise in an amount of about 1 mole to about 2 moles per mole of aluminum alkoxide, and the reactants heated about 30 minutes to about 2 hours at about 40° C. to about 90° C. The reaction mixture is then cooled and the solvent removed.

The present invention also relates to the use of the essentially pure acid hydroxyl ligand aluminum complexes as antacids and in the use of such antacids in the treatment of hyperacidity.

The essentially pure acid hydroxyl ligand aluminum complexes of the the present invention have a high acid neutralization capacity (ANC) of at least 5 mEq/g and a reduced interaction with phosphate in the GI tract. The acid hydroxyl ligand aluminum complexes under simulated GI tract conditions are found to precipitate less than 53% of the available phosphate while aluminum hydroxide wet gel is found to precipitate 63.4% of the available phosphate.

The acid hydroxyl ligand aluminum complexes once prepared may be stored for future use or formulated with conventional additives that is pharmaceutically acceptable carriers commonly used with antacid compositions to form antacid compositions for oral ingestion. The acid hydroxyl ligand aluminum complexes can be used alone or in combination with other active ingredients such as milk powders and milk fractions; antiflatulents such as simethicone; antacids such as magnesium carbonate, calcium carbonate, magnesium bicarbonate, calcium bicarbonate, sodium bicarbonate, aluminum hydroxide, aluminum phosphate, magnesium hydroxide, magnesium trisilicate, aluminum magnesium trisilicate hydrate, sodium aluminum silicate, calcium phosphates such as mono, di and tribasic, ground limestone, ground oyster shells and the like; plant extracts such as carrageenan, alginic acid and the like. The acid hydroxyl ligand aluminum complexes can be used in a method for treating a physiological condition in a mammalian body that is benefited from treatment with an antacid which comprises administering to said mammalian body an antacid effective quantity of at least one acid hydroxyl ligand aluminum complex alone or in combination with a pharmaceutically acceptable carrier.

The antacid compositions may be prepared to offer a variety of textures to suit particular applications. Such compositions may be in the form of a lozenge, tablet, toffee, nougat, chewy candy, chewing gum, suspension, and so forth. The pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and absorbents in order to prepare a particular antacid composition. The preparation of confectionery and chewing gum products is well known and does not constitute an essential aspect of this invention.

As used herein, the term confectionery material means a product containing a bulking agent selected from a wide variety of materials such as sugar, corn syrup and in the case of sugarless bulking agents sugar alcohols such as sorbitol and mannitol and mixtures thereof. Confectionery material may include such exemplary substances as lozenges, tablets, toffee, nougat, chewy candy and so forth. In general, the bulking agent will comprise from about 5 to about 99% and preferably about 20 to about 95% by weight of the antacid confectionery product.

Lozenges are flavored dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweeteners, acidulents, colorants and so forth may also be added.

Boiled candy lozenges may also be prepared from nonfermentable sugar alcohols such as sorbitol mannitol, and hydrogenated corn syrup. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particulate materials and are formed intro structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc. By comparison, the high boiling syrup, or "bob syrup," is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY: Science and Technology*, 2nd edition, AVI Publishing Co., Inc., Westport, Conn., (1980), at pages 424–425, which disclosure is incorporated herein by reference.

Pharmaceutical suspensions of this invention may be prepared by conventional methods long established in the art of pharmaceutical compounding. Suspensions may contain conventional adjunct materials employed in formulating the suspensions of the art. The suspensions of the present invention can comprise:

(a) preservatives such as benzoic acid, sorbic acid, methylparaben, propylparaben and ethylenediaminetetracetic acid (EDTA). Preservatives are generally present in amounts up to about 1% and preferably from about 0.05 to about 0.5% by weight of the suspension;

(b) buffers such as citric acid-sodium citrate, phosphoric acid-sodium phosphate, and acetic acid-sodium acetate in amounts up to about 1% and preferably from about 0.05 to about 0.5% by weight of the suspension;

(c) suspending agents or thickeners such as cellulosics like methylcellulose, carageenans like alginic acid and its derivatives, xanthan gums, gelatin, acacia, and microcrystalline cellulose in amounts up to about 20% and preferably from about 1% to about 15% by weight of the suspension;

(d) antifoaming agents such as dimethyl polysiloxane in amounts up to about 0.2% and preferably from about 0.01 to about 0.1% by weight of the suspension;

(e) sweeteners includes those sweeteners both natural and artificial well known in the art.

Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the suspension. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the suspension;

(f) flavorants include both natural and artificial flavors, and mints such as peppermint, menthol, vanilla, artificial vanilla, chocolate, artificial chocolate, cinnamon, various fruit flavors, both individual and mixed may be utilized in amounts from about 0.5% to about 5% by weight of the suspension;

(g) colorants useful in the present invention include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, and known as F.D.& C. dyes and the like. Such dyes are generally present in amount up to about 0.25% and preferably from about 0.05% to about 0.2% by weight of the suspension;

(h) decolorizing agents such as sodium metabisulfite, ascorbic acid and the like may be incorporated into the suspension to prevent color changes due to aging. In general, amounts up to about 0.25% and preferably 0.05% to 0.2% by weight of the suspension are used;

(i) solubilizers such as alcohol, propylene glycol, polyethylene glycol and the like may be used to solubilize the flavors. Solubilizing agents are generally present in amounts up to about 10%; preferably from about 2% to about 5% by weight of the suspension.

Pharmaceutical suspensions of the present invention may be prepared as follows:

(A) admixing the thickener with water heated from about 40° C. to about 95° C. preferably about 40° C. to about 70° C. to form a dispersion if the thickener is not water soluble or a solution if the thickener is water soluble, (B) admix the sweetener with water to form a solution, (C) admix the acid hydroxyl ligand aluminum complex with the thickener-water admixture to form a uniform thickener-adsorbate composition, (D) combine the sweetener solution with the thickener-adsorbate composition and mix until uniform.

(E) admix optional ingredients such as colorants, flavors, decolorants, solubilizers, antifoaming agents, buffers and additional water with the mixture of step (D) to form the suspension.

Pharmaceutical tablets of this invention may also be in chewable form. This form is particularly advantageous because of convenience and patient acceptance. To achieve acceptable stability and quality as well as good taste and mouth feel several considerations are important, namely amount of active substance per tablet, flavor, compressibility and organoleptic properties of the acid hydroxyl ligand aluminum complex.

The preparation of chewable medicated candy is by procedures similar to those used to make soft confectionery products. This procedure generally involves the formation of a boiled sugar-corn syrup blend to which is added a frappe mixture. The boiled sugar-corn syrup blend may be prepared from sugar and corn syrup blended in parts by weight ratio of about 90 to 10 to about 10 to 90. This blend is heated to temperatures above 121° C. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 65° C. and 121° C.

The acid hydroxyl ligand aluminum complex can then be added as the temperature of the mix is lowered to about 65° C. to about 135° C. whereupon additional ingredients are added such as flavors, and colorants. The formulation is further cooled and formed to pieces of desired dimensions.

A general discussion of the lozenge and chewable tablet forms of confectionary may be found in H. A. Lieberman and L. Lachman, *Pharmaceutical Dosage Forms*: Tablets Volume 1, Marcel Dekker, Inc., New York, N.Y., 1980, at pages 289 to 466 which disclosure is incorporated herein by reference.

As used herein, the term chewing gum product means a product containing a chewing gum formulation. In general, the chewing gum formulation will comprise from about 5 to about 99% and preferably 20% to about 95% by weight of the acid hydroxyl ligand aluminum complex chewing gum product.

With regard to a chewing gum formulation, such formulations contain a gum base and various additives, such as sweeteners and flavors. The gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the elastomer component. Such elastomer solvents may comprise methyl, glyceryl or pentaerythrityl esters of rosins or modified rosins, such as hydrogenated, dimerized or polymerized rosins or mixtures thereof. Examples of elastomer solvents suitable for use herein include the pentaerythrityl ester of partially hydrogenated wood rosin, pentaerythrityl ester of wood rosin, glyceryl ester of wood rosin, glyceryl ester of partially dimerized rosin, glyceryl ester of polymerized rosin, glyceryl ester of tall oil rosin, glyceryl ester of wood rosin and partially hydrogenated wood rosin and partially hydrogenated methyl ester of rosin, such as polymers of alpha-pinene and beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like as well as natural and synthetic waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts from about 3% to about 20% by weight of the final gum base composition.

The chewing gum composition may additionally include the conventional additives of flavoring agents, coloring agents such as titanium dioxide, emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfame-K and the like, and the free acid form of saccharin.

C. Dipeptide based sweeteners such as L-aspartyl-L-phenylalanine methyl ester and materials described in U.S. Pat. No. 3,492,131 and the like. In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amount of about 25% to about 75% by weight, and most preferably from about 50% to about 65% by weight of the final chewing gum composition. In contrast, the artificial sweeteners described in categories B and C are used in amounts of about 0.005% to about 5.0% and most preferably about 0.05% to about 2.5% by weight of the final chewing gum composition. These amounts are ordinarily necessary to achieve a desired level of sweetness independent from the flavor level achieved from flavor oils. While water may be added independently with dry sweeteners, it will generally be added as part of a corn syrup or corn syrup mixture.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition.

The colorants useful in the present invention, include the pigments which may be incorporated in amounts of up to about 6% by weight of the composition. A preferred pigment, titanium dioxide, may be incorporated in amounts of up to about 1% by weight. Also, the colorants may include other dyes suitable for food, drug and cosmetic applications, and known as F. D. & C. dyes and the like. The materials acceptable for the foregoing spectrum of use are preferably water-soluble. Illustrative examples include the indigo dye, known as F.D. & C. Blue No. 2, which is the disodium salt of 5,5-indigotindisulfonic acid. Similary, the dye known as F. D. & C. Green No. 1, comprises a triphenylmethane dye and is the monosodium salt of 4-[4-N-ethyl-p-sulfobenzylamino)diphenylmethylene]-[1-(N-ethyl-N-p-sulfonium-benzyl)-2,5-cyclohexadienimine]. A full recitation of all F. D. & C. and D. & C. colorants and their corresponding chemical structures may be found in the Kirk-Othmer Encyclopedia of Chemical Technology, 3rd Edition, in Volume 6, at pages 561-595, which text is accordingly incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

The quantity of acid hydroxyl ligand aluminum complex used may vary widely depending upon the particular complex, its ANC and the desired ANC of the pharmaceutical product. Amounts of acid hydroxyl ligand aluminum complex of about 200 to about 6,000 mg per dosage are useable dependent upon the particular complex.

The dosage range of the tricine aluminum complex would be about 375 to about 2,250 mg per dose. The dosage range of the threonine aluminum complex would be about 320 to about 1,950 mg per dose.

The present invention is further illustrated by the following examples. All parts and percentages in the examples and throughout the specification and claims are by weight of the final composition unless otherwise indicated.

EXAMPLE 1

This Example demonstrates the formation of acid hydroxyl ligand aluminum complexes of this invention.

The following procedure was followed to prepare each of the acid hydroxyl ligand aluminum complexes listed in Tables 1 and 2.

To a solution of aluminum isopropoxide containing ½ mole of aluminum isopropoxide in 500ml of anhydrous isopropanol under nitrogen at 80° C. was added ½ mole of acid hydroxyl ligand with mixing. The mixture was then maintained at 80° C. for one hour. One mole of water was then added dropwise to the solution with mixing and the mixture maintained an additional 1.5 hours at 80° C. The reaction mixture was then cooled and the solvent removed by distillation at reduced pressure at a temperature less than 60° C. to yield a white powder.

TABLE 1

ANC AND MOLECULAR WEIGHT FOR INVENTIVE ACID HYDROXYL LIGAND ALUMINUM COMPLEXES

| COMPLEX NUMBER | POLYALCOHOL LIGAND (L) | Al:L RATIO | ANC (MEQ/G) LIGAND | ANC (MEQ/G) COMPLEX | ANC (EQ/MOLE) COMPLEX | MOLECULAR WEIGHT OF COMPLEX (G/MOL) |
|---|---|---|---|---|---|---|
| 1 | Pamoic Acid | 1:1 | 1.62 | 4.22 | 2.15 | 509.1 |
| 2 | Pamoic Acid | 2:1 | 1.62 | 9.35 | 5.37 | 574.1 |
| 3 | Bicine | 1:1 | 1.53 | 10.18 | 2.22 | 217.6 |
| 4 | Tricine | 1:1 | 1.36 | 13.02 | 3.06 | 234.6 |
| 5 | Threonine | 1:1 | 0.53 | 15.28 | 2.94 | 192.7 |

In tables 1, 2 and 3.
Bicine = $HO_2CCH_2N(CH_2CH_2OH)_2$
Tricine = $HO_2CCH_2NHC(CH_2OH)_3$

TABLE 2
ROSSETT-RICE AND pH STAT DATA FOR INVENTIVE ACID HYDROXYL LIGAND ALUMINUM COMPLEXES

| COMPLEX NUMBER | ACID AMINE LIGAND (L) | Al:L RATIO | ROSSETT-RICE LAG (MIN) | PEAK PH | RR TIME (MIN) | pH STAT (MINUTES) T50 | T90 |
|---|---|---|---|---|---|---|---|
| 1 | Pamoic Acid | 1:1 | 0.8 | 3.37 | 15.8 | 26.0 | >70 |
| 2 | Pamoic Acid | 2:1 | 2.0 | 3.02 | — | 65.0 | >70 |
| 3 | Bicine | 1:1 | 1.6 | 3.10 | 1.4 | >70 | >70 |
| 4 | Tricine | 1:1 | 0.0 | 4.28 | 44.2 | 1.7 | 13.5 |
| 5 | Threonine | 1:1 | 0.0 | 4.70 | 48.6 | 0.7 | 3.2 |

The acid hydroxyl ligand aluminum complexes have ANC values of from about 4 to about 15 in mEq/g and all exceed 2 Eq/mole. Aluminum hydroxide dry gel has an ANC of about 22 to 30 mEq/g and 2.2 to 2.9 Eq/mole. the method of preparation of aluminum hydroxide gel greatly effects its ANC and this accounts for the variation in test results. Complexes having an ANC greater than 5 mEq/g are preferred for use as antacids. The inventive acid hydroxyl ligand aluminum complexes of this Example all have an acceptable ANC.

Procedures

The molecular weight for each complex given in Table I was calculated by assaying the aluminum content for each complex then assuming one aluminum atom per molecule for complexes 1 to 5 and two aluminum atoms per molecule for complex 2.

Acid Neutralizing Capacity (ANC) Test Preparation: (ANC TEST <301>, p. 1192, USPXXI, Mack Pub. Co., Easton, Pa., 1984).

Transfer an accurately weighed portion of test substance to a 250 ml beaker, add 70 ml of water, and mix for 1 minute.

Procedure:

Pipet 30.0 mL of 1.0N hydrochloric acid volumetric solution into the Test Preparation while continuing the stir with the Magnetic Stirrer. Stir for 15 minutes, accurately timed, after the addition of the acid, begin to titrate immediately, and in a period not to exceed an additional 5 minutes, titrate the excess hydrochloric acid with 0.5N sodium hydroxide volumetric solution to attain a stable (for not less than 15 seconds) pH of 3.5. Calculate the number of mEq of acid consumed, and express the result in terms of mEq of acid consumed per g of the substance tested. Each mL of 1.0N hydrochloric acid is equal to 1 mEq of acid consumed.

The ANC is a static test which gives only a limited picture of the antacid behavior. Complexes were then tested for buffering capacity by the Rossett-Rice titration method and for their rate of reactivity by the pH-stat titration. These two tests are dynamic and give a more precise picture of antacid reactivity.

Briefly, the Rossett-Rice (RR) titration, N. E. Rossett, M. L. Rice, Gastroenterology, 1954, 26, 490, involves the addition of acid at a constant rate to a quantity of antacid equivalent to 26.4 mEq of ANC and monitoring the pH as a function of time. Three parameters which characterize the antacid are obtained. These are the lag time, duration (RR time) and peak pH. The lag time is the time, in minutes required for the reaction mixture to reach pH 3. The RR time is the time, in minutes, the reaction mixture remains above pH3. The peak pH is the maximum pH of the reaction mixture during the test. The pH-stat titration, N.J. Kerkoff, et al., *J. Pharm. Sci.*, 1977, 66, 1528, requires the variable addition of acid to the antacid sample (equivalent to 2 mEq of ANC) at a rate sufficient to maintain the pH at 3. This data is then plotted as the volume of acid added versus time. From this plot one can obtain two parameters which characterize the reactivity of the antacid. These are $T_{50}$ and $T_{90}$ which are the times required to neutralize 50% and 90% of the total theoretical amount of acid. The data for both tests is presented in Table 2 and shows several interesting trends. First, all complexes tested show acceptable to excellent pH-stat results. The RR data also show excellent results for all complexes. They react immediately with acid (lag time<2 min.), show good buffering ability and exceed a pH of 3.0.

EXAMPLE 2

This Example demonstrates decreased phosphate interaction of inventive acid hydroxyl ligand aluminum complexes when compared to aluminum hydroxide wet gel.

The acid hydroxyl ligand aluminum complexes in Table 3 are the same complexes prepared and tested in Example 1.

The amount of phosphate remaining in solution after treatment with acid followed by intestinal fluid was determined and the results are summarized in Table 3. A range, from 52.1 to 21.4% of added phosphate, was removed from the solution by the tested compounds. Aluminum hydroxide wet gel removed 63% of the phosphate added. All of the compounds tested showed improvements over aluminum hydroxide in terms of not precipitating phosphate; i.e., more than 47% of the added phosphate remained in the solution. Aluminum hydroxide wet gel, the major active ingredient in many commercially available antacid preparations, was used as a reference. This gel reacts with hydrochloric acid in the stomach to produce water soluble aluminum chloride which undergoes subsequent hydrolysis to form a hydrated hydroxy aluminum complex. In the small intestine, this aluminum complex reacts with dietary phosphate to form water insoluble phosphate salts. In order to examine the phosphate interaction properties of the inventive compounds as they pass through the gastrointestinal tract, all compounds were subjected to reaction with hydrochloric acid (physiological acid strength) before reacting with phosphate.

The Rossett-Rice titration was used to condition each of the compounds before reaction with phosphate. This titration attempts to simulate in-vivo stomach for evaluating the effectiveness of an antacid formulation. Different antacids vary markedly in their in vivo and in vitro potency and it has therefore been recommended that antacid dosage be determined according to milliequivalents of neutralizing capacity rather than volume or number of tablets of different antacids. A standardized sample weight of 3.6 g was used in this study. The experimental method is as follows:

A pourable slurry containing 3.6 g of the test compound was introduced into an acidic solution of pH about 1.6 at 37° C. Simultaneously, 0.1N HCl was added at a constant rate of 4 mL/min for 15 minutes. The period of fifteen minutes is the gastric residence time suggested by the OTC panel, Federal Register #65, 1973, 38, 8717. After reaction with acid, the mixture was treated with intestinal fluid T.S. (pH=7.5) which is 0.05M in phosphate. The amount of intestinal fluid added was calculated to deliver one mole of phosphate per mole of aluminum. The pH of the suspension was constantly monitored and it was observed that, for certain compounds, the mixture remained very acidic after the intestinal fluid was added. In order to simulate in vivo conditions, 1.0N sodium hydroxide was added to bring the pH of the final suspension to 7.0.

The suspension was stirred for 15 minutes and then centrifuged. An aliquot of the supernatant was analyzed for phosphate and the amount of phosphate remaining in solution was calculated.

The amount of phosphate remaining in solution is summarized in Table 3.

TABLE 3

Phosphate Interaction of Inventive Acid Amine Ligand Aluminum Complexes and Aluminum Hydroxide Wet Gel.

| Complex Number | Polyalcohol Ligand (L) | Ratio Al:L | Phosphate Remaining (%) |
|---|---|---|---|
| 1 | Pamoic Acid | 1:1 | 47.9 |
| 2 | Pamoic Acid | 2:1 | 60.4 |
| 3 | Bicine | 1:1 | 78.6 |
| 4 | Tricine | 1:1 | 78.0 |
| 5 | Threonine | 1:1 | 56.4 |
| Aluminum hydroxide wet gel | | | 36.6 |

The invention being thus described, it will be obvious that the same may be varied in many ways. Such variations are not to be regarded as a departure from the spirit and scope of the invention and all such modifications are intended to be included within the scope of the following claims.

We claim:

1. A method for treating a physiological condition in a mammalian body that is benefited from treatment with an antacid which comprises administering to said mammalian body an antacid effective quantity of at least one essentially pure complex of an acid hydroxyl ligand and aluminum having an acid neutralization capacity of at least 5 mEq/g and the formula:

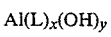

wherein:
X=0.5 or 1
Y=2 and
L is an acid hydroxyl ligand wherein the acid hydroxyl ligand is selected from the group consisting of serine, homoserine, threonine, tyrosine, hydroxyproline, bicine, tricine and hydroxylysine when x=1 and pamoic acid when x=0.5.

2. A method in accordance with claim 1 wherein the antacid complex is administered orally.

3. A method in accordance with claim 1 wherein the physiological condition is or is accompanied by hyperacidity.

4. An antacid composition comprising
   (a) an antacid effective quantity of at least one essentially pure complex of a acid hydroxyl ligand and aluminum having the formula:

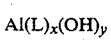

wherein:
x=0.5 or 1
y=2, and
L is a acid amine ligand and
   (b) a pharmaceutically acceptable carrier.

5. The antacid composition of claim 4 wherein the essentially pure acid amine ligand and aluminum complex has an acid neutralization capacity of at least 5 mEq/g and the molar ratio of acid amine ligand to aluminum in the complex is from about 1:1 to about 1:2.

6. A method for treating a physiological condition in a mammalian body that is benefited from treatment with an antacid which comprises administering to said mammalian body an antacid effective quantity of at least one composition of claim 4.

7. A method in accordance with claim 6 wherein the antacid composition is administered orally.

* * * * *